United States Patent [19]

Boyd

[11] Plant 4,869

[45] Jul. 27, 1982

[54] WHITE FLOWERING DOGWOOD—WORLD'S FAIR VARIETY

[75] Inventor: J. Austin Boyd, McMinnville, Tenn.

[73] Assignee: The Boyd Brothers Company, McMinnville, Tenn.

[21] Appl. No.: 244,078

[22] Filed: Mar. 16, 1981

[51] Int. Cl.[3] ..... A01H 5/00

[52] U.S. Cl. ..... Plt./51

[58] Field of Search ..... Plt./51

*Primary Examiner*—James R. Feyrer

*Attorney, Agent, or Firm*—Burns, Doane, Swecker & Mathis

[57] ABSTRACT

A new and distinct variety of white Flowering Dogwood, botanically known as *Cornus florida* is provided. The new variety most nearly resembles the native Flowering Dogwood, but primarily is distinguished therefrom by a compact and upright growth habit, stocky trunk and strong stubby limbs of relatively large diameter, and the abundant formation of attractive white blossoms which often are present in closely disposed clusters. The new variety was named in honor of the World Energy Fair to be held at Knoxville, Tenn. during 1982.

2 Drawing Figures

SUMMARY OF THE INVENTION

The new and distinct variety of white Flowering Dogwood tree was discovered in the fall of 1974 while growing near Highway No. 55 within a block of approximately 100,000 *Cornus florida* trees on the cultivated nursery property of the assignee located six miles from McMinnville, Tenn. The seed which yielded the block of *Cornus florida* was obtained from native white Flowering Dogwood trees and had been planted during the fall of 1973. Accordingly, the new variety is believed to be a chance seedling or mutation of unknown parentage which differs from all prior known dogwood tree varieties of which I am aware.

At the time of my discovery my attention was attracted to a single tree in the seedling block which was significantly different in appearance from all other trees in the block. This tree also was different than all other dogwood trees I have observed during the past twenty-five years. Steps were taken by me carefully to preserve and to continue to observe the new variety following its discovery.

The new variety has been found to possess the following novel combination of characteristics:

(1) a compact and upright growth habit, (2) stocky trunk, (3) strong limbs of relatively large diameter, (4) the display of attractive white blossoms often in relatively closely disposed clusters, (5) the display of more white blossoms than the Cloud 9 variety (U.S. Plant Pat. No. 2,112) and the Imperial White variety (U.S. Plant Pat. No. 4,242), (6) the display of white blossoms which are slightly smaller than those of the Cloud 9 variety and the Imperial White variety, (7) the display of white blossoms approximately one one week later than the Cloud 9 variety, (8) good hardiness, and (9) improved resistance to drought.

Asexual reproduction by budding at the nursery of the assignee beginning in 1975 confirmed that the distinctive appearance of the new variety comes true and is established and transmitted through succeeding propagations.

The new and distinctive variety of dogwood tree has been named the World's Fair variety in honor of the World Energy Fair to be held at Knoxville, Tenn. during 1982.

BRIEF DESCRIPTION OF PHOTOGRAPHS

The photographs show a typical specimen of the new variety when approximately three years of age while grown at McMinnville, Tenn. The photographs were obtained during April 1979 and depict the plant in color as nearly true as it is reasonably possible to make the same in a color illustration of this character.

DETAILED DESCRIPTION OF NEW VARIETY

Figure 1:
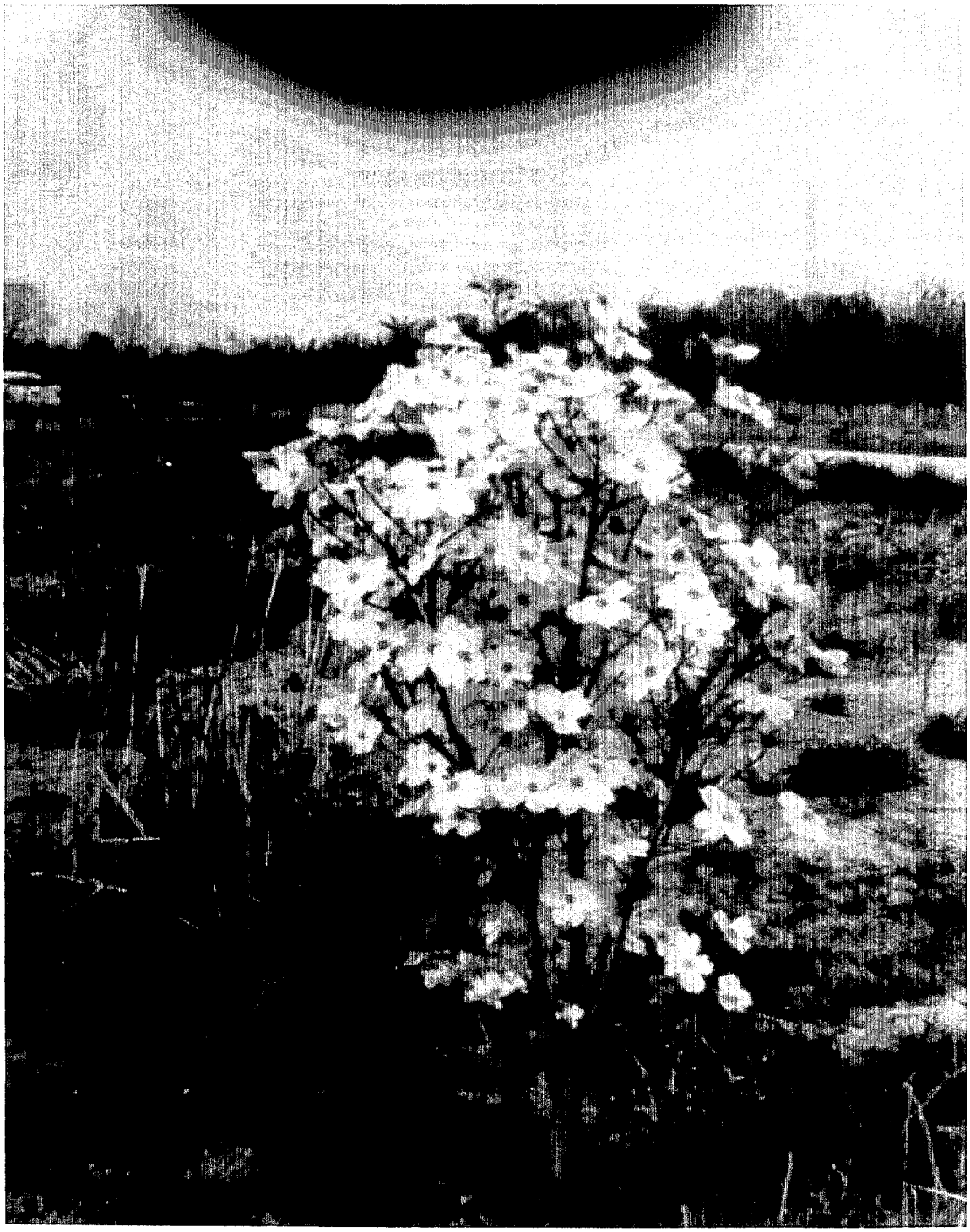
FIG. 1 illustrates the overall appearance of the plant wherein the general growth habit, stocky trunk, and strong stubby limbs of relatively large diameter are apparent.
Figure 2:
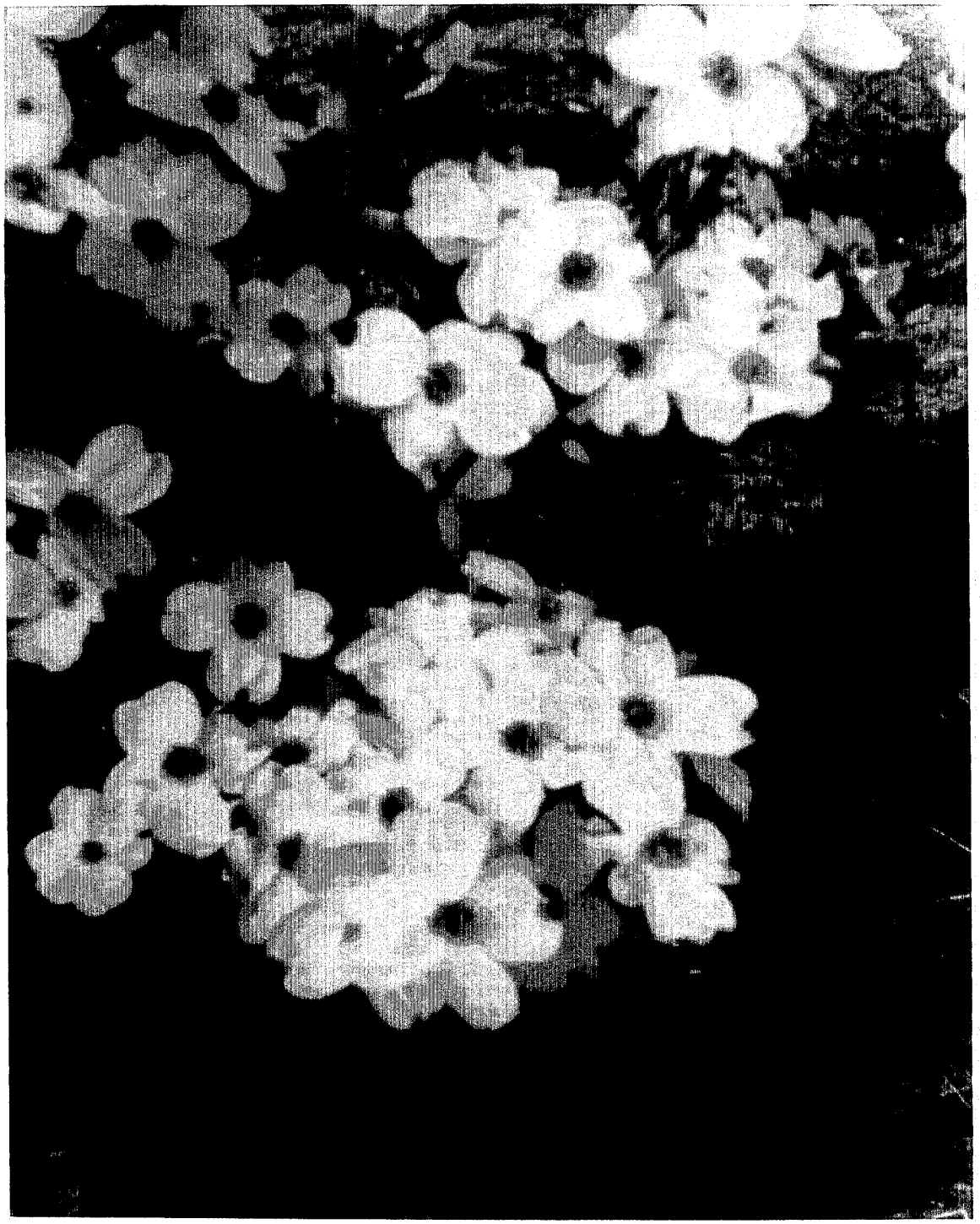
FIG. 2 illustrates the attractive white blossoms of the variety which tend often to be displayed in relatively closely disposed clusters.

The following description was made of plants growing at McMinnville, Tenn. Color terminology is to be accorded its ordinary dictionary significance. Unless otherwise stated the new variety has characteristics substantially identical to those of the native white Flowering Dogwood.

Growth habit: Upright with compact relatively uniform crown.

Trunk and branches: The trunk is stocky and tends to be of larger caliper than other dogwood varieties. The trunk of a one year old tree of the present variety measured 2 to 3 inches above the ground will tend to be approximately 7/16 inch in diameter while that of the native white Flowering Dogwood will tend to be approximately 5/16 inch. The limbs of the new variety possess a distinctive stubby appearance and are strong and of a relatively large diameter. The stocky branches are light green in color when young and turn dark gray when mature.

Blossoms: The blossoms are highly attractive and commonly appear approximately one week later than the Cloud 9 variety. A typical date for first blooming is about Apr. 10th to 15th, but later if weather is cool and earlier if weather is warmer than usual. The white bracts form blossoms which tend to be borne in relatively closely disposed clusters of 3 to 5 or more blossoms unlike the individual blossoms commonly formed on the native white Flowering Dogwood. However, some single or individual blossoms will be observed on the present variety. The blossoms commonly measure approximately 4½ to 5 inches in diameter during a normal growing year and tend to be slightly smaller than those of the Cloud 9 variety and the Imperial White variety. The blossoms tend to be formed in more abundance than those of the Cloud 9 variety and the Imperial White variety.

Foliage: Typical leaves commonly measure approximately 3½ inches in width and 5½ inches in length. Such leaves tend to be smaller than those of the Cloud 9 variety and the Imperial White variety. The leaf color is a slightly darker green than the Cloud 9 variety, and the leaves tend to be more glossy on the upper surface than the native white Flowering Dogwood, the Cloud 9 variety, and the Imperial White variety.

Silvical characteristics: The new variety survived the winter of 1977–1978 when the temperature stayed below freezing for approximately forty days. The new variety also has withstood temperatures of −10° F. without damage. Improved drought resistance also has been demonstrated when compared with most other dogwood trees. Such drought resistance was particularly demonstrated during time period of May 29, 1980 to Nov. 10, 1980, when the area experienced considerably less than usual amount of precipitation.

I claim:

1. A new and distinct variety of white Flowering Dogwood tree, botanically known as *Cornus florida,* substantially as illustrated and described, characterized particularly as to novelty by the unique combination of (1) a compact and upright growth habit, (2) stocky trunk, (3) strong limbs of relatively large diameter, (4) the display of attractive white blossoms often in relatively closely disposed clusters, (5) the display of more white blossoms than the Cloud 9 variety and the Imperial White variety, (6) the display of white blossoms which are slightly smaller than those of the Cloud 9 variety and the Imperial White variety, (7) the display of white blossoms approximately one week later than the Cloud 9 variety, (8) good hardiness, and (9) improved resistance to drought.

* * * * *